(12) United States Patent
Sarajlic

(10) Patent No.: US 12,286,344 B2
(45) Date of Patent: Apr. 29, 2025

(54) METHOD OF MANUFACTURING A MICRO-FLUID PROBE

(71) Applicant: CYTOSURGE AG, Glattbrugg (NL)

(72) Inventor: Edin Sarajlic, Zutphen (NL)

(73) Assignee: CYTOSURGE AG, Glattbrugg (NL)

( * ) Notice: Subject to any disclaimer, the term of this patent is extended or adjusted under 35 U.S.C. 154(b) by 141 days.

(21) Appl. No.: 18/249,262

(22) PCT Filed: Oct. 14, 2021

(86) PCT No.: PCT/EP2021/078397
§ 371 (c)(1),
(2) Date: Apr. 17, 2023

(87) PCT Pub. No.: WO2022/079145
PCT Pub. Date: Apr. 21, 2022

(65) Prior Publication Data
US 2023/0391613 A1 Dec. 7, 2023

(30) Foreign Application Priority Data
Oct. 15, 2020 (NL) ........................................ 2026676

(51) Int. Cl.
*B81C 1/00* (2006.01)
*G01Q 70/16* (2010.01)

(52) U.S. Cl.
CPC ...... *B81C 1/00111* (2013.01); *B81C 1/00087* (2013.01); *B81B 2201/12* (2013.01); *B81B 2203/0353* (2013.01); *B81C 2201/0132* (2013.01); *B81C 2201/0133* (2013.01); *B81C 2201/0198* (2013.01); *G01Q 70/16* (2013.01)

(58) Field of Classification Search
CPC ............. B81C 1/00111; B81C 1/00087; B81C 2201/0132; B81C 2201/0133; B81C 2201/0198; B81B 2201/12; B81B 2203/0353; G01Q 70/16; A61M 2037/003; A61M 2037/0053; A61M 37/0015
See application file for complete search history.

(56) References Cited

U.S. PATENT DOCUMENTS

| 11,174,155 | B2* | 11/2021 | Sarajlic | B81C 1/00087 |
| 2017/0247243 | A1* | 8/2017 | Berenschot | B81B 1/004 |
| 2017/0247252 | A1* | 8/2017 | Sarajlic | B81C 1/00119 |

OTHER PUBLICATIONS

International Search Report mailed Apr. 21, 2022 issued in connection with International Application No. PCT/EP2021/078397 (3 pages total).
International Search Report mailed Apr. 22, 2022 issued in connection with International Application No. PCT/EP2021/078397 (7 pages total).

* cited by examiner

*Primary Examiner* — Anita K Alanko
(74) *Attorney, Agent, or Firm* — Tatonetti IP

(57) ABSTRACT

A method of manufacturing a micro-fluidic probe that is relatively simple comprises providing a pyramidal pit in a substrate with a structural layer. Then metal masking layers using directionally depositing are provided. The angles of deposition are chosen such that for one deposition step the walls are covered but at least one wall is left less or not exposed, whereas for the other deposition said at least one wall is covered except for a bottom section thereof. Thus these deposited layers can be used as masks for etching the structural layer.

8 Claims, 10 Drawing Sheets

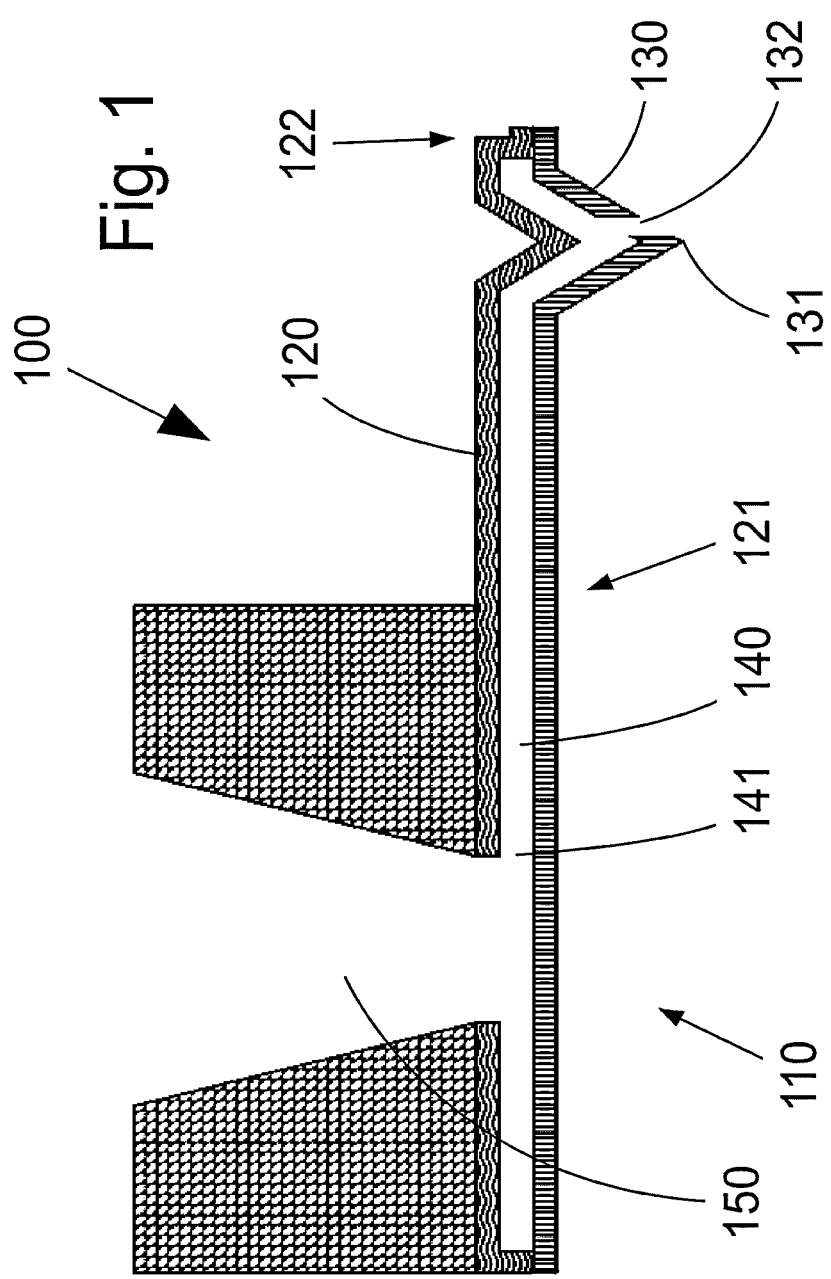

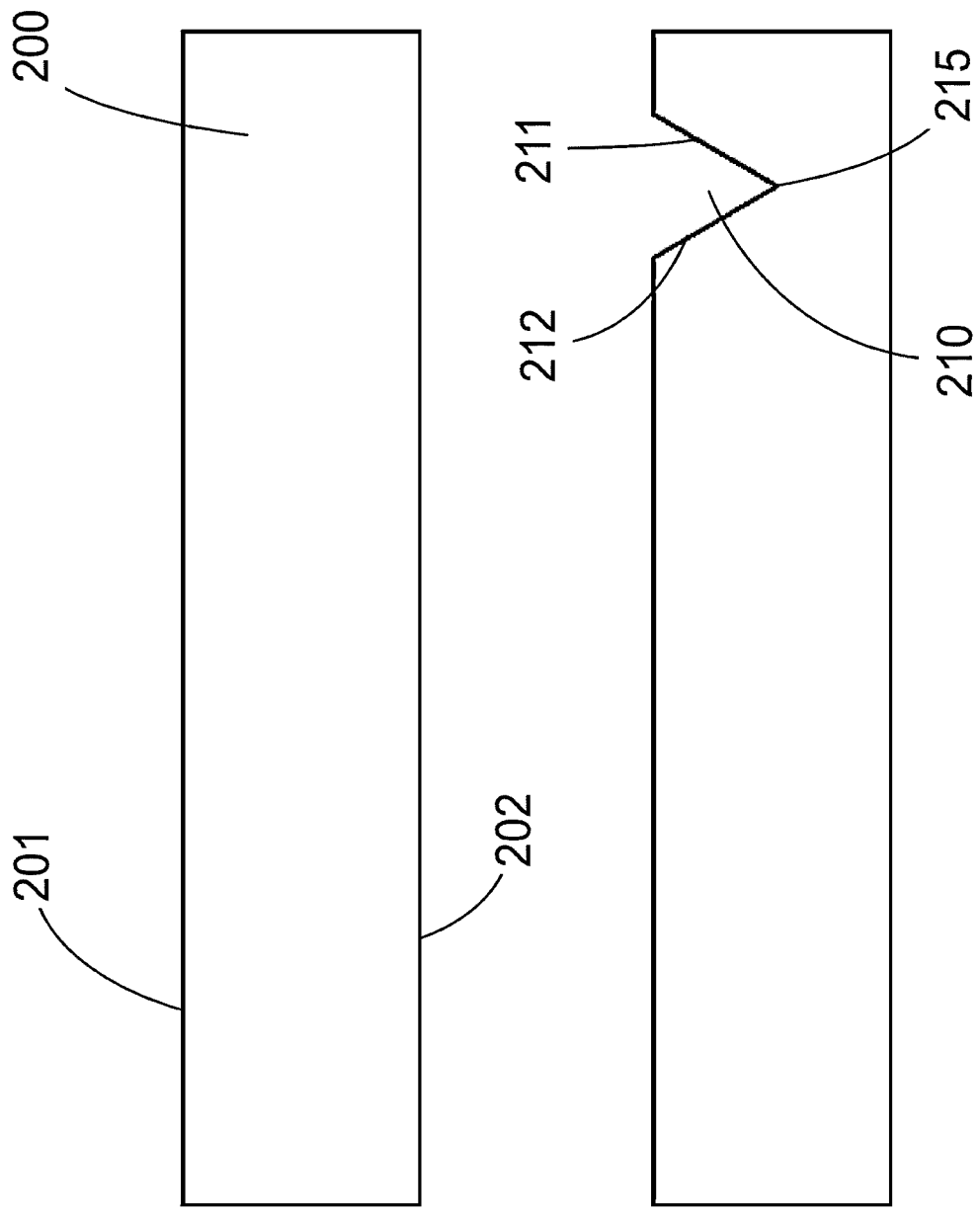

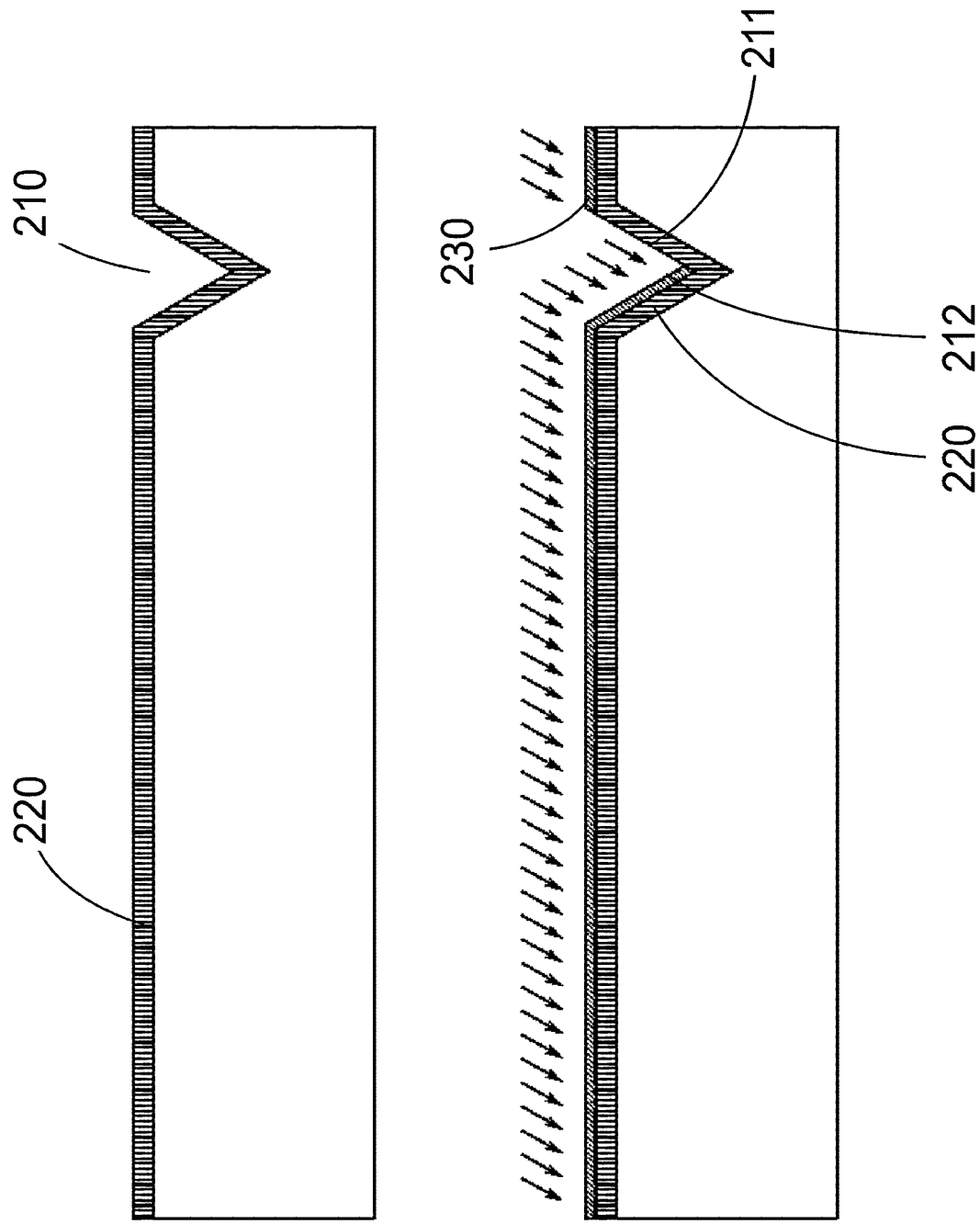

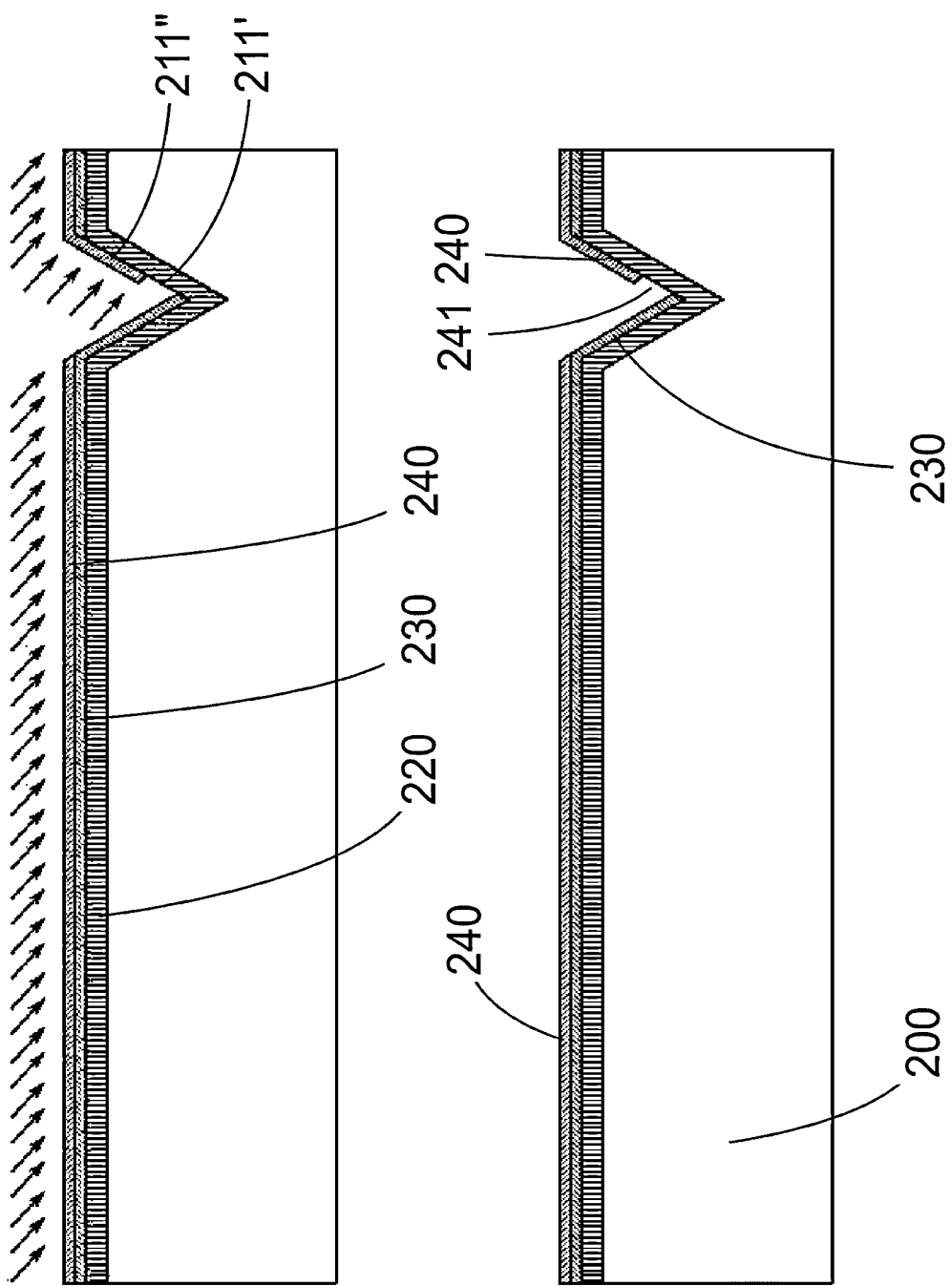

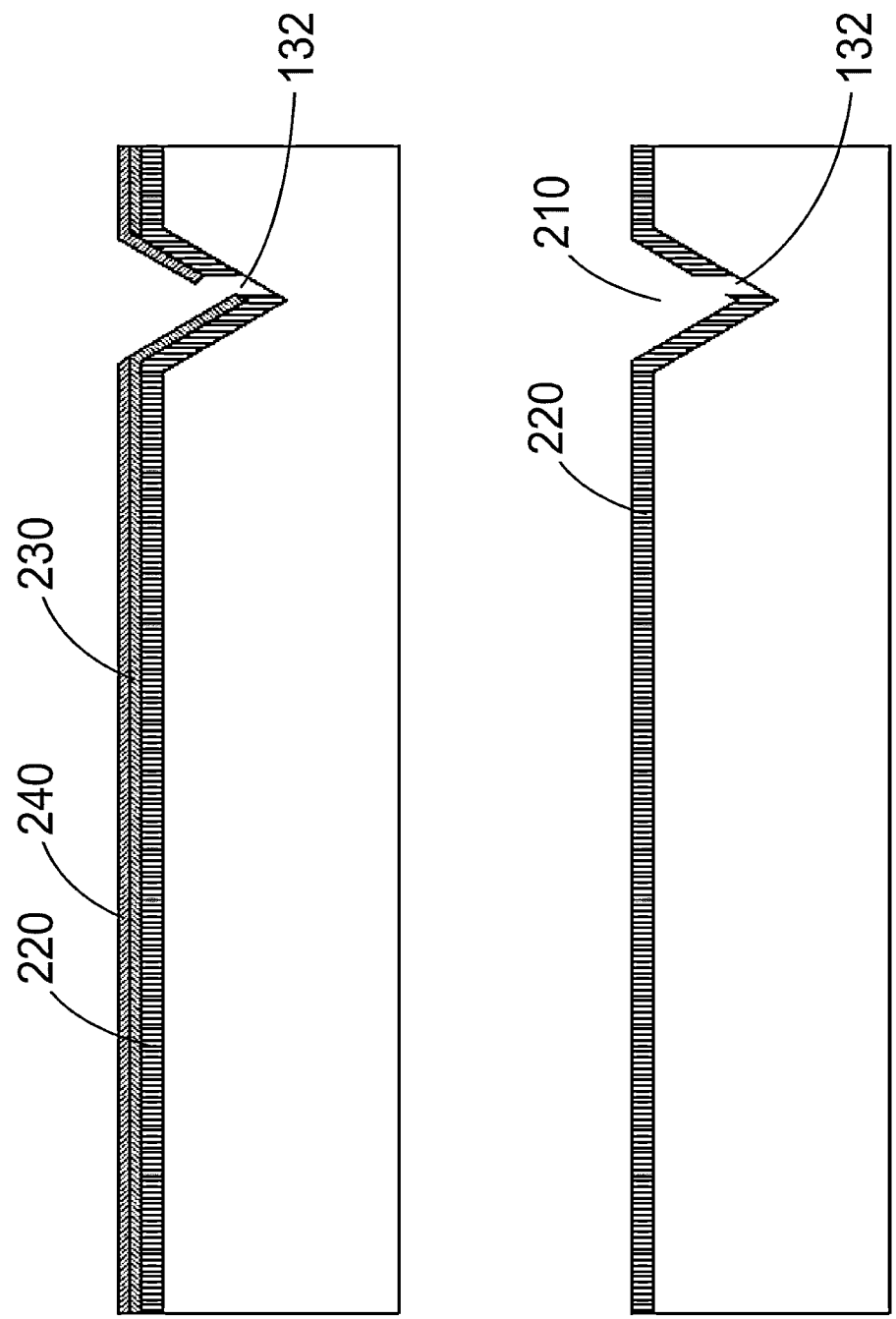

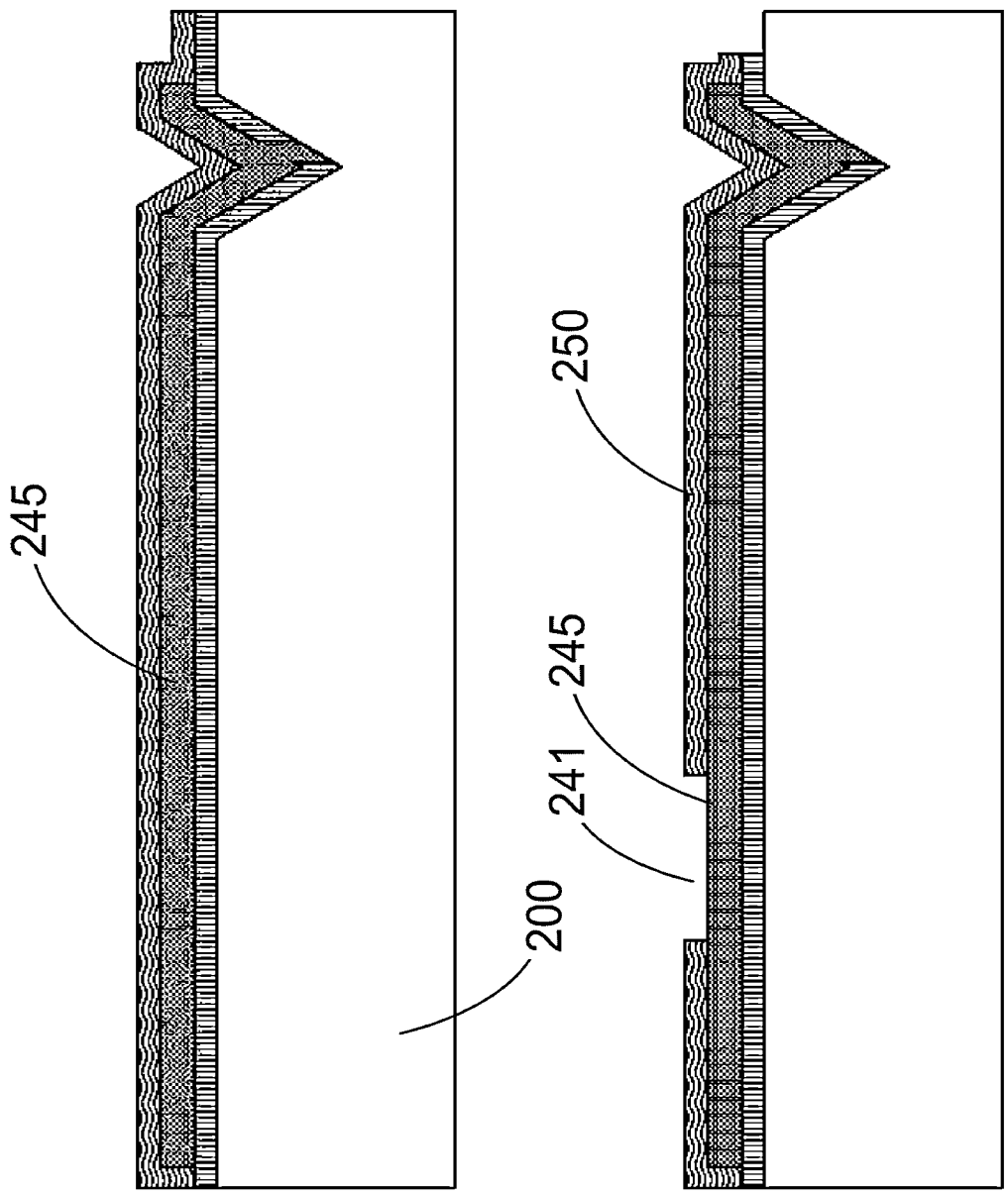

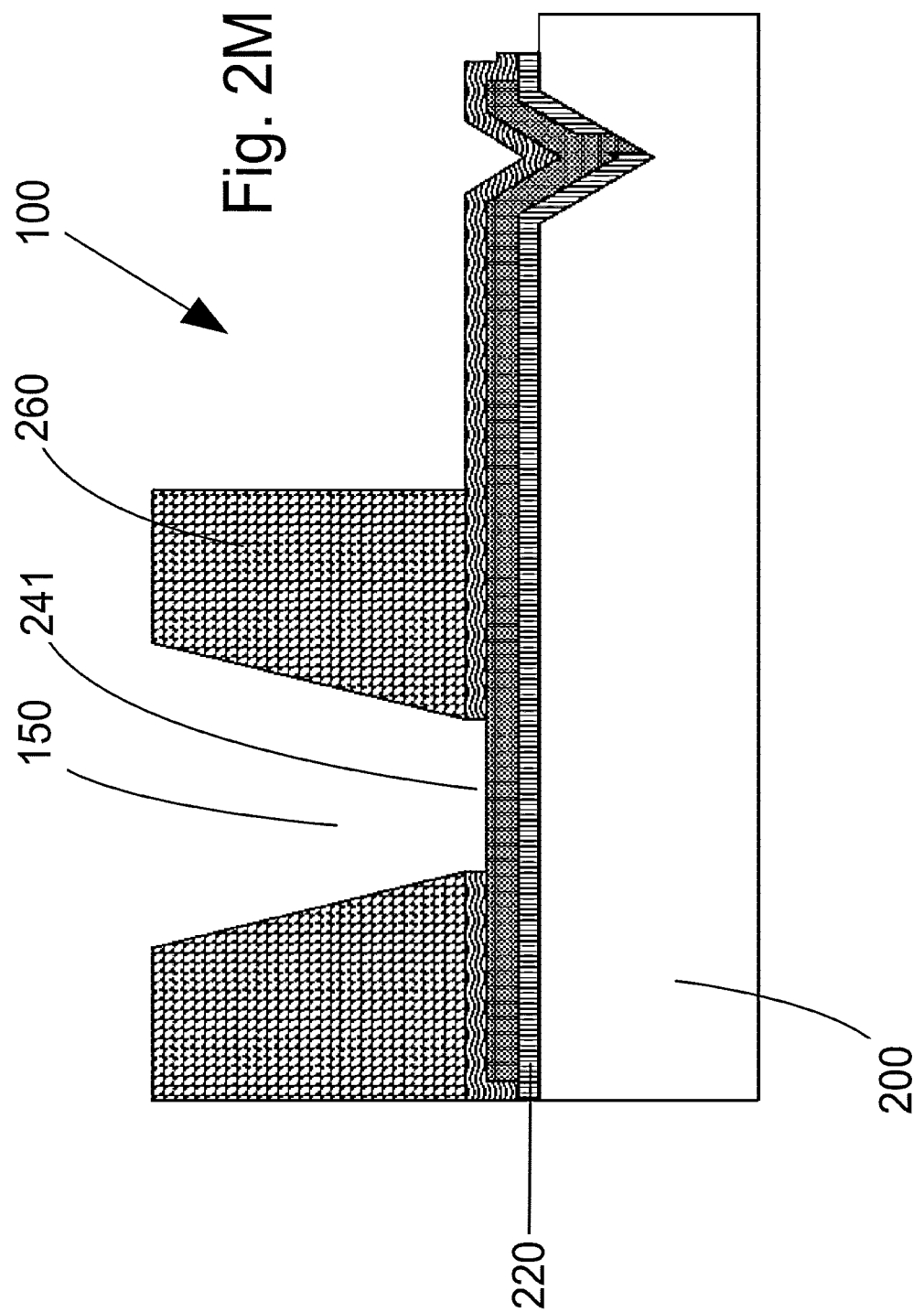

METHOD OF MANUFACTURING A MICRO-FLUID PROBE

CROSS-REFERENCES TO RELATED APPLICATIONS

This Non-Provisional Patent application claims the benefit of and priority to PCT Application Serial No. PCT/EP2021/078397, entitled "A Method of Manufacturing a Micro-Fluid Probe," filed Oct. 14, 2021, which claims the benefit of and priority to Netherlands Patent Application Serial No. 2026676, entitled "A Method of Manufacturing a Micro-Fluid Probe," filed Oct. 15, 2020, the entire contents of both applications of which are hereby incorporated herein by reference.

BACKGROUND

The present invention relates to a method of manufacturing a micro-fluidic probe.

Various MEMS devices, such as probes comprising a hollow cantilever, comprise at least one through-hole in a layer of first material such as silicon nitride. The through-hole is for example in a face of a pyramidal tip of the cantilever of a MEMS probe. MEMS probes comprising hollow cantilevers having a tip are used in life sciences for a variety of purposes, two of them being the delivery of a substance to or extraction of material from a cell. In that case, the tip of the MEMS probe will have to penetrate through the cell wall. Material of the cell wall should not clog the opening at the tip of the probe. For this reason, preference is given to probes having the opening (through-hole) in a side wall or pyramidal edge (i.e. a hole in two adjacent side walls) of the tip, instead of at the tip's distal end. In the art, probes with a cantilever comprising a conduit and having a tip are routinely produced.

EP3210937 discloses a method of manufacturing a plurality of through-holes in a layer of material, allowing for the manufacture of a micro-fluidic probe.

In said method, a pyramidal pit is created in a silicon substrate, and the surface of the silicon substrate is covered with silicon nitride. The silicon nitride layer is covered with layer of silicon oxide and provided with a hole at the bottom of the pit using corner lithography. Subsequently, a metal layer (chromium) is deposited at an angle, causing the silicon oxide layer to act as a shadow masking layer, leaving a spot at the bottom of the pit on a sidewall thereof free of chromium and leaving silicon nitride exposed. The silicon nitride is subsequently etched so as to form a through-hole.

This method is effective yet relatively complicated.

SUMMARY

The object of the present invention is to provide a method with reduced complexity.

To this end, a method according to the preamble is characterized in that an intermediate product is subjected to a plurality of method steps, the intermediate product
- defining a first side and a second side, and
- comprises a base substrate, said base substrate comprising a base material, wherein at the first side the surface of the base substrate defines a main plane;
- wherein the plurality of method steps comprises the steps of
- providing the base substrate of the intermediate product at the first side with a plurality of pyramidal pits in said base material, a pyramidal pit comprising i) a first pyramidal side at an angle α to the main plane and ii) further pyramidal planes,
- providing the base substrate with a layer of first material at the first side of the intermediate product, the first material being different from the base material so as to result in the intermediate product having pits comprising a layer of said first material, in arbitrary order
- directionally depositing a second layer of a second material different from the first material, said second material being a material capable of being deposited directionally and said directional depositing being performed in a first direction relatively parallel with the first pyramidal side so as to deposit said second layer on the further pyramidal sides wherein said second layer on each of the further pyramidal sides is thicker than the thickness of any second material deposited on the first pyramidal side, and
- directionally depositing a third layer of a third material different from the first
- material on the first side, said third material being a material capable of being deposited directionally and said directional depositing being performed in a second direction, said second direction
- being relatively transverse to the first pyramidal side at an angle R to the main plane, said angle R having an absolute value smaller than the absolute value of a, and
- having a vectorial component parallel to the main surface that is opposite to
- the vectorial component parallel to the main surface of the first direction; i.so as to deposit said third layer on a top section of the first pyramidal side while an
- edge of the pyramidal pit serves as a shadow mask so as to shield a bottom section of the first pyramidal side from being covered with said third material; and
- etching the exposed parts of the layer of said first material using the second layer of second material and the third layer of third material as a masking layer to provide a through-hole in the layer of first material.

Thus, the layer of first material is exposed at an area (the first section) off-center to the central location (nadir) of the pyramidal pit and subjected to etching at the exposed off-center location, as a result of which the through-hole is formed in said layer of first material. Subsequent removal of base material at the location of the pit will result in the through-hole being accessible from both the first side and the second side.

An example of a material that can be deposited directionally is silicon dioxide (https://www.lesker.com/newweb/deposition_materials/depositionmaterials_evaporationmaterials_1.cfm?pgid=si2).

In the present application, the base substrate will in general be a wafer. The wafer is for example a silicon wafer, which may be used to manufacture probes comprising four-sided or three-sided pyramidal pits, as desired, depending on the crystal orientation of the starting wafer with respect to the base main plane. For four-sided and three-sided pyramidal tips these are 100 and 111 silicon respectively.

The method according to the invention requires fewer method steps and the size of the through-hole can be controlled by selecting the angle fr Smaller angles θ lead to larger through-holes.

After locally penetrating the layer of first material, the method will be continued using any conventional steps for manufacturing the MEMS device that is desired. By way of example, for a probe comprising a hollow conduit, a sacrificial conduit layer will be provided, followed by further wall material for the conduit covering said sacrificial conduit layer, and etching to remove the sacrificial conduit layer material, so as to result in a hollow conduit. Removing crystalline base material at the location of the pyramidal pit will result in a freely extending cantilever. Such methods are known in the art, for example from WO2012/096571.

The angle $\alpha$ is typically determined by the type of silicon chosen. For 100 silicon, this angle will be 54.74°.

The step of etching may be performed using wet etching, although for improved process control dry etching will in general be preferred.

Typically the silicon substrate is removed in a step later than the step of etching the first layer to form the through-hole.

A MEMS device manufactured according to the present invention may for example be used for taking a sample from a cell, or introducing material into a cell.

According to a favourable embodiment, the second material and the third material are the same.

This allows for efficient production of probes.

According to a favourable embodiment, at least one of the second material and the third material is a metal, preferentially chromium. A metal can be conveniently deposited directionally through vaporization. Chromium is in particular suitable as a masking metal. According to a favourable embodiment, the step of etching comprises directional dry etching, preferably Reactive Ion Etching (RIE).

This allows to further control the formation of the through-hole.

According to a favourable embodiment, the method further comprises after the step of etching part of the layer of first material using the second layer of second material and the third layer of third material as a masking layer to form the through-hole a step of removing said second layer and third layer.

Thus after serving their purpose as protective layers during etching of the through-hole, these helper layers are removed.

According to a favourable embodiment, the method comprises further steps for manufacturing a plurality of microfluidic probes wherein each probe of the plurality of probes comprises
a probe base section—having a probe base main plane, and
comprising a first opening of a conduit; and
a cantilever protruding from said probe base section parallel with the probe base main plane, said cantilever having
a proximal end connected to the probe base section, and a distal cantilever end;
said cantilever comprising a tip having a distal tip end, said tip comprising a second opening
of said conduit at a location away from the distal tip end;
wherein the second opening is a through-hole that is formed by at least one step comprising the step of etching part of the layer of said first material using the second layer of second material and the third layer of third material as a masking layer.

MEMS probes are an important application area and for the state of the art forming the second opening (the through-opening) in a face (side wall) of the tip, i.e. not at the terminal point of the tip, is a major cost factor because so far they had to be milled individually with accurate aiming of a focused ion beam. The present invention does not require ion beam milling individual tips. The term "in a face" does not exclude that the hole is in two adjacent faces, i.e. crossing a pyramidal ridge.

According to a favourable embodiment, the base material is a crystalline base material, and before the base substrate is provided with the layer of first material, the method comprises the step of etching the base substrate at the first side to form a plurality of pits in said crystalline base material, the pits comprising the first pyramidal face that is at the angle $\alpha$ to the main plane.

Pits are typically formed using anisotropic etching of the base material, which allows for the formation of pyramidal pits. Thus MEMS techniques allow for the manufacture of probes having a sharp pyramidal tip. With a probe comprising a sharp tip, excessive damage to the cell can to be avoided. The probe may also serve a dual role, because the tip may be used for scanning using one of a variety of scanning techniques known in the art. A typical crystalline base material used in the art is silicon (1, 0, 0).

The face will extend along a crystal plane of the base material.

The step of providing the first layer may be preceded by treating the pyramidal pit so as to result in sharper tips, for example using the method disclosed by S. Akamine and C; F. Quate (J. Vac. Sci. Technolg. B 10(5) (1992) p. 2307-2310).

According to a favourable embodiment, before the step of etching the exposed parts of the layer of said first material using the second layer of second material and the third layer of third material as a masking layer, the second layer of second material is partially etched to expose the layer of first material.

Thus it may be ensured that no masking material remains at the location where the first material is to be etched.

BRIEF DESCRIPTION OF THE DRAWINGS

The present invention will now be illustrated with reference to the drawing where FIG. 1 shows a probe as can be manufactured using the method according to the invention, in a cross-sectional view;

FIG. 2A to FIG. 2M illustrate a method of manufacturing the probe according to FIG. 1 in a cross-sectional view;

DETAILED DESCRIPTION

Figure 2I:
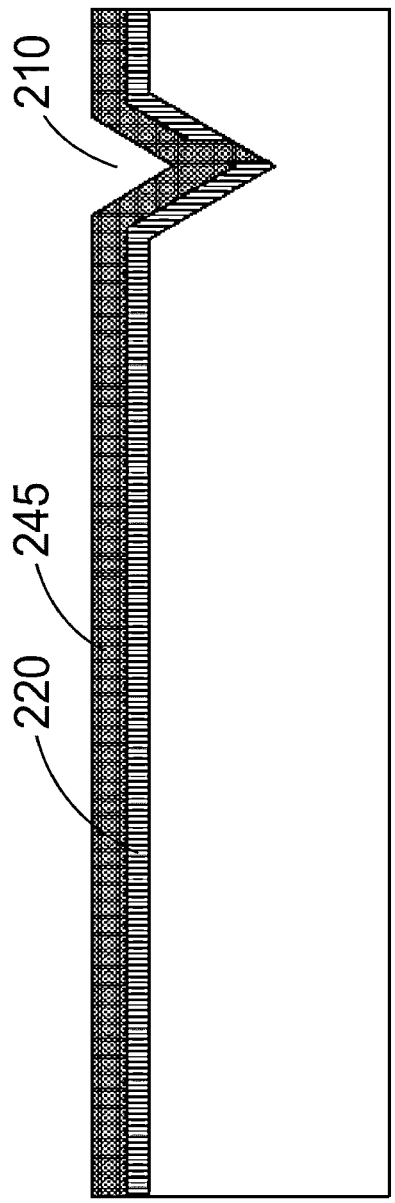

The probe 100 comprises a probe base section 110 and a cantilever 120 extending from the probe base section 110. The cantilever 120 has a proximal end 121 connected to the probe base section 110 and a distal cantilever end 122.

The distal cantilever end 122 comprises a pyramidal tip 130 comprising a pyramidal tip end 131. In a face of the pyramidal tip 130, i.e. away from the pyramidal tip end 131, there is a through-hole 132 manufactured in accordance with the present invention.

The probe 100 comprises an elongated conduit 140 extending from a reservoir 150 at the probe base section 110 through the cantilever 120 to the through-hole 132.

The conduit 140 comprises a first opening 141 and the second opening is defined by the through-hole 132.

The method according to the invention will now be illustrated using FIG. 2A to FIG. 2M, which show in a cross-sectional side view a method of manufacturing the probe 100 of FIG. 1. The method according to the present invention allows for a multitude of through-holes 132 and hence probes 100 to be manufactured at once, but the figures will show one probe 100 in the making only.

A silicon wafer 200 having a thickness of 380 um is shown (FIG. 2A) in a cross-sectional view. The silicon wafer 200 used as base substrate 200 is of single crystal (1, 0, 0) silicon. If a pyramidal tip with three faces is desired, (1, 1, 1) silicon may be used instead.

The silicon wafer is a base substrate 200 having a first side 201 and a second side 202. The first side 201 of the silicon wafer defines a main base plane.

Using a mask, pyramidal pits 210 (only one shown, singulars are used in the remainder of the figure description) are etched by wet anisotropic etching of the silicon using 25% KOH (FIG. 2B) at 75° C. The pyramidal pit 210 is 9 um×9 um. The nadir 215 is about 6.5 um from the main plane.

After the KOH etching the masking layer is removed in a concentrated HF solution (49%).

A thin layer of first material 220 (400 nm), here silicon nitride, is deposited (FIG. 2C) on the silicon wafer 200 comprising the pyramidal pit 210 (FIG. 2C) by Low Pressure Chemical Vapor Deposition (LPCVD). Silicon-rich nitride (SiRN) is used due to its low intrinsic mechanical stress. The silicon nitride is a structural layer that will be part of a wall defining the conduit 140 and the pyramidal tip 130.

Figure 3A:
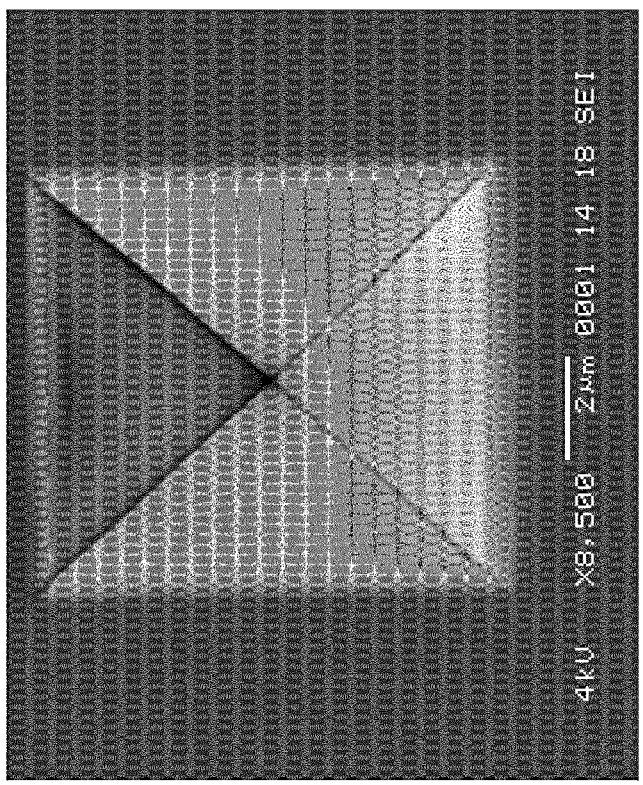
FIG. 3a shows a Scanning Electron Microscope image of a probe manufactured according to the invention.

The intermediate product of the previous step is provided with a protective layer 230 (100 nm chromium on a reference surface outside the water. The actual thickness on the pyramidal tip sides is less due to the angle, and this thickness is not critical) using a directional depositing technique (FIG. 2D). We used evaporation at an angle to the main silicon wafer plane of 55°. The vapor flux is almost parallel with a first pyramidal side 211 of the pyramidal pit 210. This means that the thickness of the evaporated material on the first pyramidal side will be drastically smaller compared with the other pyramidal sides 212 due to the directionality of the evaporation process. For example, if we evaporate a layer with a thickness t(0) at an angle perpendicular to the plane (evaporation angle is 90°), then the thickness of the deposited material on an inclined side with an angle alpha to the normal given by:

$t(alpha)=t(0)*cos(alpha)$. This means that even if we have an deviation in the evaporation angle (in the ideal situation you need an angle of 54.34° to be parallel with the inclined side of the first pyramidal side) of for example 2°, there will still be 28 times less material on the first pyramidal sides compared to the perpendicular plane. FIG. 3A shows a SEM photo of this stage.

The wafer 200 provided with the second layer of second material 230 (chromium; 100 um) is provided with a third layer of a third material 240 (again 100 nm chromium) using a directional depositing technique (FIG. 2E). Now, however from a second direction and at an angle chosen such that a bottom section 211' of the first pyramidal side remains in the shadow whereas chromium is deposited at a top section 211". The size of the bottom section depends on the evaporation angle beta. We have chosen an evaporation angle of 47.5°.

On the bottom section 211' close to the nadir 215 of the pyramidal pit 210 a rather thin layer of the protective material (chromium) is deposited during the first inclined evaporation (not shown in the figures). A short etch of 20 seconds (etch rate is around 60 nm/min) is performed to completely remove chromium from this area (FIG. 2F). We use commercially available chromium etchant Selectipur (containing ammonium cerium (IV) nitrate as the main active component). Note that chromium on other areas of the pit 210 is preserved because the thickness was larger. A SEM photo of this stage is shown in FIG. 3A.

The intermediate product of the previous step is etched using Reactive Ion Etching (ME). The silicon nitride layer 220 in the bottom section 211' not protected by the masking (chromium) layers is etched through to create a through-hole 132 on the first pyramidal side 211 close to the nadir 215 of the pyramidal pit 210 (FIG. 2G). After the ME etching the protective layer (chromium) is selectively and completely removed using chromium etchant (Selectipur) (FIG. 2H).

Figure 2J:
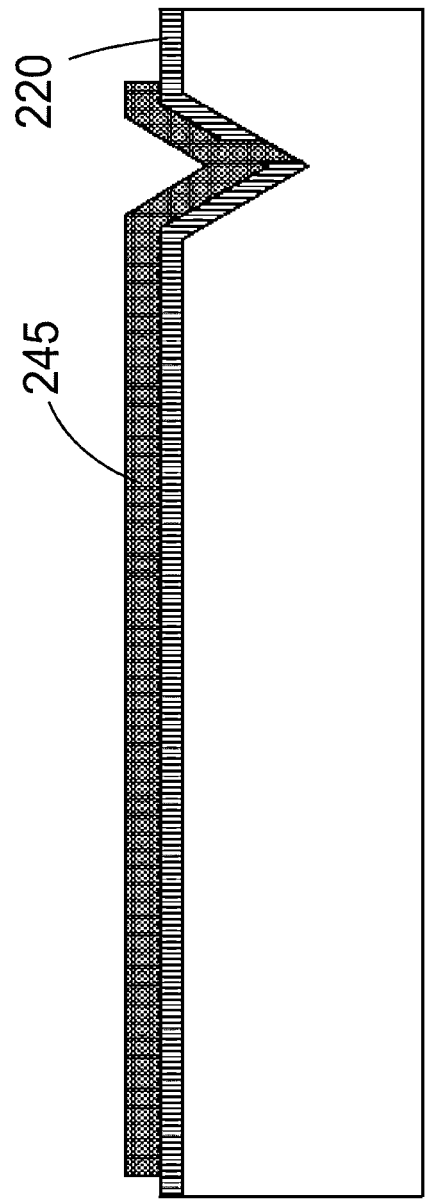

The remainder of the probe 100 is manufactured according to well-known practices, by providing the intermediate product obtained in the previous step with a layer of sacrificial material 245, here polycrystalline silicon (FIG. 2I) with a thickness of 1.5 um, which is subsequently patterned by RIE (FIG. 2J).

A 400 nm thick layer 250 of silicon nitride is deposited by LPCVD, encapsulating the sacrificial polysilicon material 245 (FIG. 2K). This silicon nitride layer 250 forms the top wall of the cantilever 120 and the micro-fluidic channel 140.

The silicon nitride layer 240 is patterned by ME. The layout of the probe 100 is defined in this processing step. Also an etching window 241 is created to expose a part of the sacrificial layer 245 at a location that will later on be at the probe base section 110 (FIG. 2L).

The silicon nitride layer 240 is bonded to a glass cover 260 by anodic bonding (FIG. 2M). The glass cover 260 has a reservoir 150 (a through-hole) that will allow access of etchant to the polycrystalline sacrificial material at the location of the cover hole 261 and, once the silicon of the wafer has been etched away, at the through-hole 132.

Thus, etching with Tetramethylammonium hydroxide (TMAH) results in the probe 100, shown in FIG. 1, while the sacrificial polysilicon layer 245 is removed creating the conduit 140 and a hollow cantilever 120 with the syringe-like tip 130.

FIG. 3A shows a Scanning Electron Microscope image of the pit as shown in FIG. 2D, for an angle alpha of 55°.

The first pyramidal side is the triangle at the top, which is substantially free of chromium because the edge of the pit serves as a shadow mask.

The further pyramidal sides to the right, left and bottom have been coated with one layer of chromium.

Figure 3B:
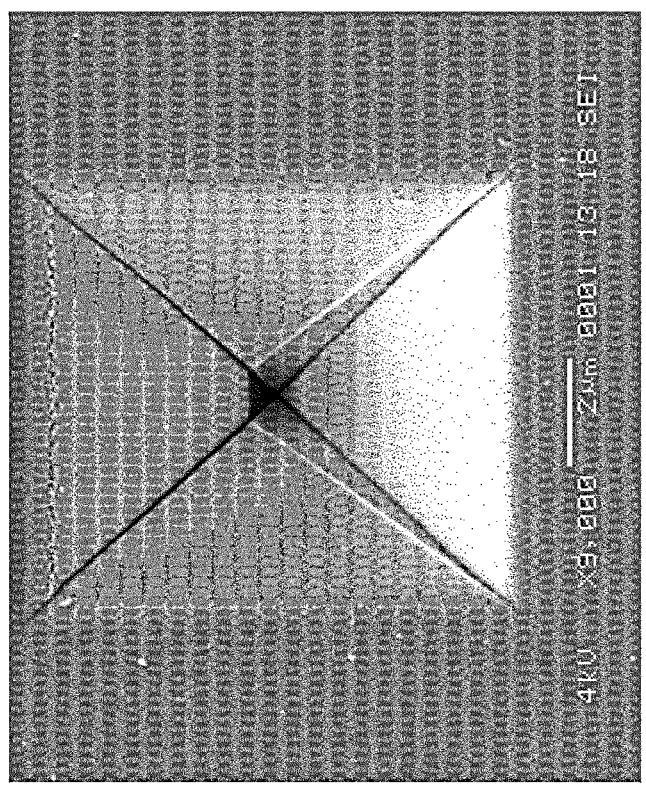
FIG. 3b shows a detail of the probe of FIG. 3A.

FIG. 3B shows a Scanning Electron Microscope image of the pit as shown in FIG. 2F, for an angle beta of 47.5°.

The first pyramidal side is the triangle at the top, showing a small black tip which is free of chromium.

The further pyramidal sides to the right and left show signs of having been subjected to chromium deposition twice. The further pyramidal side at the bottom has been coated with only one layer of chromium.

The invention claimed is:

1. A method of manufacturing a micro-fluidic probe, wherein an intermediate product is subjected to a plurality of method steps, the intermediate product:
   defining a first side and a second side, and
   comprises a base substrate, said base substrate comprising a base material, wherein at the first side the surface of the base substrate defines a main plane;
wherein the plurality of method steps comprises the steps of:
   providing the base substrate of the intermediate product at the first side with a plurality of pyramidal pits in said base material, a pyramidal pit comprising i) a first pyramidal side at an angle α to the main plane and ii) further pyramidal planes, providing the base substrate with a layer of first material at the first side of the intermediate product, the first material being different from the base material so as to result in the intermediate product having pits comprising a layer of said first material, in arbitrary order directionally depositing a second layer of a second material different from the first material, said second material being a material capable of being deposited directionally and said directional depositing being performed in a first direction relatively parallel with the first pyramidal side so as to deposit said second layer on the further pyramidal sides wherein said second layer on each of the further pyramidal sides is thicker than the thickness of any second material deposited on the first pyramidal side, and directionally depositing a third layer of a third material different from the first material, on the first side, said third material being a material capable of being deposited directionally and said directional depositing being performed in a second direction, said second direction being relatively transverse to the first pyramidal side at an angle β to the main plane, said angle β having an absolute value smaller than the absolute value of α, and having a vectorial component parallel to the main surface that is opposite to the vectorial component parallel to the main surface of 11 the first direction;

so as to deposit said third layer on a top section of the first pyramidal side while an edge of the pyramidal pit serves as a shadow mask so as to shield a bottom section of the first pyramidal side from being covered with said third material; and etching the exposed parts of the layer of said first material using the second layer of second material and the third layer of third material; as a masking layer to provide a through-hole in the layer of first material.

2. The method of claim 1, wherein the second material and the third material are the same.

3. The method of claim 2, wherein at least one of the second material and the third material is a metal, preferentially chromium.

4. The method of claim 3, wherein the step of etching comprises directional dry etching, preferably Reactive Ion Etching (RIE).

5. The method of claim 4, wherein the method further comprises after the step of etching part of the layer of first material using the second layer of second material and the third layer of third material as a masking layer to form the through-hole a step of removing said second layer and third layer.

6. The method of claim 5, wherein the method comprises further steps for manufacturing a plurality of micro-fluidic probes wherein each probe of the plurality of probes comprises a probe base section having a probe base main plane, and comprising a first opening of a conduit; and a cantilever protruding from said probe base section parallel with the probe base main plane, said cantilever having a proximal end connected to the probe base section, 12 and a distal cantilever end;

said cantilever comprising a tip having a distal tip end, said tip comprising a second opening of said conduit at a location away from the distal tip end;

wherein the second opening is a through-hole that is formed by at least one step comprising the step of etching part of the layer of said first material using the second layer of second material and the third layer of third material as a masking layer.

7. The method of claim 6, wherein the base material is a crystalline base material, and before the base substrate is provided with the layer of first material, the method comprises the step of etching the base substrate at the first side to form a plurality of pits in said crystalline base material, the pits comprising the first pyramidal face that is at the angle α to the main plane.

8. The method of claim 7, wherein before the step of etching the exposed parts of the layer of said first material using the second layer of second material and the third layer of third material as a masking layer, the second layer of second material is partially etched to expose the layer of first material.

* * * * *